United States Patent
Gemba et al.

(12)

(10) Patent No.: US 6,214,855 B1
(45) Date of Patent: Apr. 10, 2001

(54) METHOD FOR THE TREATMENT OF STROKE USING N-HETEROCYCLIC GLYOXLYAMIDE COMPOUNDS

(75) Inventors: Takefumi Gemba, Hyogo; Yozo Hori, Osaka, both of (JP)

(73) Assignee: Shionogi & Co., Ltd., Osaka (JP)

( * ) Notice: Subject to any disclaimer, the term of this patent is extended or adjusted under 35 U.S.C. 154(b) by 0 days.

(21) Appl. No.: 09/402,084

(22) PCT Filed: Apr. 23, 1998

(86) PCT No.: PCT/JP98/01880

§ 371 Date: Sep. 29, 1999

§ 102(e) Date: Sep. 29, 1999

(87) PCT Pub. No.: WO98/47508

PCT Pub. Date: Oct. 29, 1998

(30) Foreign Application Priority Data

Apr. 24, 1997 (JP) ................................................ 97-01421

(51) Int. Cl.⁷ .......................... A61K 31/40; A61K 31/405
(52) U.S. Cl. .............................................. 514/413; 514/415
(58) Field of Search ...................................... 514/413, 415

(56) References Cited

U.S. PATENT DOCUMENTS

| | | | |
|---|---|---|---|
| 5,271,940 | 12/1993 | Cleary et al. | 424/448 |
| 5,296,222 | 3/1994 | Petersen et al. | 424/94 |
| 5,654,326 | 8/1997 | Bach et al. . | |

FOREIGN PATENT DOCUMENTS

| | | | |
|---|---|---|---|
| 0 675 110 A1 | * 3/1995 | (EP) . | |
| 0675110 | 10/1995 | (EP) . | |
| 95/33462 | 12/1995 | (WO) . | |
| 96/03383 | 2/1996 | (WO) . | |
| WO 96/03383 | * 2/1996 | (WO) . | |

OTHER PUBLICATIONS

Berg et al., "Pharmaceutical Salts", J. of Pharm. Sci., 66:1–19, 1977.

Hans Bundgaard, "Design of Prodrugs", pp. 6–25, 1985.

Clark et al., "Preparation of Indoles and Oxindoles from N–(tert–Butoxycarbonyl)–2–alkylanilines", Synthesis Papers, pp. 871–878, 1991.

Shen and Winter, "Chemical Properties of Metabolites" pp. 176–177 (No Date Available).

Desideri et al., "Synthesis of 3–hydroxy–2–pyridineacetic acid and its evaluation on experimental lipaemia" Eur. J. Med Chem. pp. 295–299, 1983.

Umemura et al., Evaluation of the Combination of a Tissue–type plasminogen activator, SUN9216, and a Thromboxane A₂ receptor antagonist, vapiprost, in a rat middle cerebral artery thrombosis model, Stroke 24:1077–1082, 1993.

\* cited by examiner

*Primary Examiner*—Raymond Henley, III
(74) *Attorney, Agent, or Firm*—Foley & Lardner

(57) ABSTRACT

A method and composition for the treatment and/or prevention of stroke is disclosed using N-heterocyclic glyoxamide compounds having the following general formula:

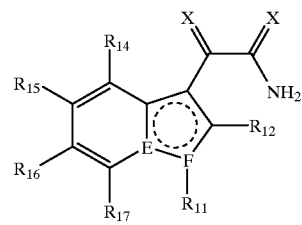

wherein X, E, F, $R_{11}$, $R_{12}$, $R_{14}$, $R_{15}$, $R_{16}$ and $R_{17}$ are as defined herein.

43 Claims, No Drawings

METHOD FOR THE TREATMENT OF STROKE USING N-HETEROCYCLIC GLYOXLYAMIDE COMPOUNDS

This is a 371 of PCT/JP98/01880 filed Apr. 23, 1998.

TECHNICAL FIELD

This invention relates to the use of N-heterocyclic glyoxylamide compounds for the treatment of stroke.

BACKGROUND ART

This invention is directed to reducing or preventing nerve cell death and subsequent neurological dysfunction normally occurring in a stroke.

Strokes are a major cause of death and disablement. Multiple mechanisms may cause stroke. Hemorrhagic stroke occurs when rupture of an artery in the brain causes a hemorrhage (viz., an aneurysm). Occlusive stroke occurs when a thrombosis or embolism restrict blood flow to part of the brain. For occlusive stroke the reduction of blood flow leads to death of brain tissue. Thrombosis occurs when a blood clot forms and blocks blood flow in an artery supplying blood to the brain. Embolism occurs when a moving clot settles in an artery supplying blood the brain, causing a stroke.

Many of those affected with strokes never recover full neurologic function or even a substantial measure of the neurologic function initially lost.

Conventional treatment consists of controlling blood pressure, administration, of blood thinners, and etc. None of the presently used techniques or therapeutic agents is without drawbacks. A great need remains to develop new methods of treating occlusive stroke by the use of improved therapeutic agents.

DISCLOSURE OF INVENTION

It is an object of this invention to provide a method of treatment of a mammal, including a human, currently afflicted with a stroke or previously afflicted with a stroke, said method comprising administering to said mammal a therapeutically effective amount of an N-heterocyclic glyoxylamide compound.

It is also an object of this invention to use an N-heterocyclic glyoxylamide compound for the manufacture of a medicament for treating stroke in a mammal, including a human, currently afflicted with a stroke or previously afflicted with a stroke.

It is also an object of this invention to provide a composition for treatment of a stroke in a mammal, including a human, currently afflicted with a stroke or previously afflicted with a stroke, said composition comprising administering to said mammal a therapeutically effective amount of an N-heterocyclic glyoxylamide compound.

It is also an object of this invention to provide a method of reducing the occurrence of neuronal damage and associated neurological dysfunction in a stroke in a human compared to that which normally occurs by administering a therapeutically effective amount of an N-heterocyclic glyoxylamide compound.

It is also an object of this invention to use N-heterocyclic glyoxylamide compounds to reduce neurological degeneration such as can be induced by a stroke and the associated functional impairment which can result in a human by administering a therapeutically effective amount of an N-heterocyclic glyoxylamide compound.

It is also an object of this invention to provide a composition of reducing the occurrence of neuronal damage and associated neurological dysfunction in a stroke in a human compared to that which normally occurs by administering a therapeutically effective amount of an N-heterocyclic glyoxylamide compound.

The term "stroke" is used herein to mean occlusive stroke, e.g., an ischemic event, resulting in the loss of oxygen supply to the brain caused by means inclusive of thrombosis or embolism.

The term, "subject" is used herein to mean mammals including, humans.

BEST MODE FOR CARRYING OUT THE INVENTION

Treatment can be remedial or therapeutic as by administering an N-heterocyclic glyoxylamide compound following an ischemic event to mitigate the effects of that event. Treatment can also be prophylactic or prospective by administering a compound in anticipation that an ischemic event may occur, for example, in a patient who is prone to stroke.

Cells known to be destroyed during a stroke include hippocampal neurons, cortical neurons, caudate and putaminous neurons, cerebellar neurons and brain stem neurons. Since these hippocampal neurons are known to be the most sensitive to strokes, the therapeutically effective amount of N-heterocyclic glyoxylamide compound is preferably a hippocampal neuron protecting amount, i.e., an amount which reduces hippocampal neuron death compared that which would occur if the stroke were untreated.

(A) Procedure for Subjects During or Soon After a Stroke:

Treatment for a subject currently afflicted with a stroke using the method of the invention should occur within 6 hours of onset of the stroke, preferably within 4 hours, and most preferably as soon as stroke diagnosis occurs. In order to obtain a rapid response with minimum risk, the administration of the N-heterocyclic glyoxylamide compound, for example, 1H-indole-3-glyoxylamide compound or indolizine compound should preferably be via a parenteral route in a neuronal cell protecting amount (i.e., an amount which reduces neuronal cell death compared to that which would occur if the stroke were not treated).

In general, N-heterocyclic glyoxylamide compound will be administered to a mammal such as man so that an effective dose is received, for example an intravenous dose in the range of about 0.1 to about 10 mg/kg of body weight.

(B) Procedure for Subjects in Danger of a Stroke:

Treatment of a subject for prevention of a stroke, where the subject is determined to be at a high risk for a stroke, but who does not currently have a stroke, is to provide a level of N-heterocyclic glyoxylamide compound such that on the occurrence of cerebral ischemia, there will be sufficient N-heterocyclic glyoxylamide compound already present in the subject to protect neuronal cells (i.e., an amount which would reduce neuronal cell death compared to that which would occur if a stroke occurred and was untreated). Administration of N-heterocyclic glyoxylamide compound is preferably carried out orally on a daily basis.

Since the occurrence of ischemia could come at any time, therapeutically sufficient plasma levels of N-heterocyclic glyoxylamide compound should be present. In general, the plasma level of N-heterocyclic glyoxylamide compound is a non-toxic concentration in the range of from about 0.01 micromolar to 1000 micromolar. The amount administered to obtain such plasma level depends on the method of administration and the half-life of the N-heterocyclic glyoxylamide compound. Preferably, administration is on a daily basis so that the dose of N-heterocyclic glyoxylamide compound can be minimized.

General Aspects of the Method:

It will be apparent to those skilled in the art that a compound of the present invention can be co-administered with other therapeutic or prophylactic agents and/or medicaments that are not medically incompatible therewith.

The regimen for treatment may stretch over many months or years so oral dosing is preferred for patient convenience and tolerance. With oral dosing, one to three oral doses per day, each from about 0.01 to about 50 mg/kg of body weight are used with preferred doses being from about 0.04 to about 5.0 mg/kg.

The specific dose of N-heterocyclic glyoxylamide compound administered according to this invention to obtain therapeutic or prophylactic effects will, of course, be determined by the particular circumstances surrounding the case, including, for example, the compound administered, the route of administration, the size and age of the patient, the severity of the stroke, and the condition being treated. Typical daily doses will contain a non-toxic dosage level of from about 0.01 mg/kg to about 50 mg/kg of body weight of an active compound of this invention.

Method of Administration.

This can be by any method such as parenteral or oral dosing wherein the N-heterocyclic glyoxylamide compound crosses the blood brain barrier in sufficient amount to protect neuronal cells from death. The N-heterocyclic glyoxylamide compounds are most often used in the method of the invention in the form of pharmaceutical formulation, as described infra. Other forms of administration may be used in both human and veterinary contexts. Such alternative forms include the use of suppositories, transdermal patches, and compositions for buccal or nasal administration, for example lozenges, nose drops, an aerosol spray, or transdermal patch.

Compound Used in the Stroke Treatment Method

The method for treating subjects for the occurrence or prevention of stroke comprises administering an effective amount of an N-heterocyclic glyoxylamide compound. Suitable 1H-indole-3-glyoxylamide compounds for the practice of the method of treating and preventing stroke as taught herein are those described in European Patent Application No. 95302166.4, Publication No. 0 675 110 (publ., Oct. 4, 1995). Suitable 1H-indole-3-glyoxylamide compounds are also those disclosed in U.S. patent application Ser. No. 08/469,954 filed Jun. 6, 1995, the disclosure of which is incorporated herein by reference. Formulations containing these 1H-indole-3-glyoxylamide compounds and methods of making them are also fully described in European Patent Office Publication European Patent Application No. 95302166.4 and U.S. patent application Ser. No. 08/469,954. Suitable indolizine compounds are disclosed in WO 9603383 (Publ., Feb. 8, 1996).

Definitions:

The words, "acid linker" refers to a divalent linking group symbolized as, -($L_a$)- or -(La')-, which has the function of joining the 4 or 5 position of the indole nucleus or the 7 or 8 position of the indolizine nucleus to an acidic group in the general relationship:

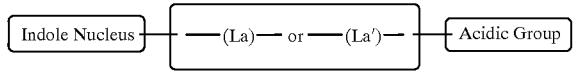

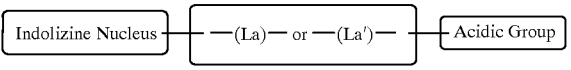

The words, "acid linker length", refer to the number of atoms (excluding hydrogen) in the shortest chain of the linking group -($L_a$)- or -(La')- that connects the 4 or 5 position of the indole nucleus or the 7 or 8 position of the indolizine nucleus with the acidic group.

The word "acidic group" is selected from -5-tetrazolyl, $-SO_3H$,

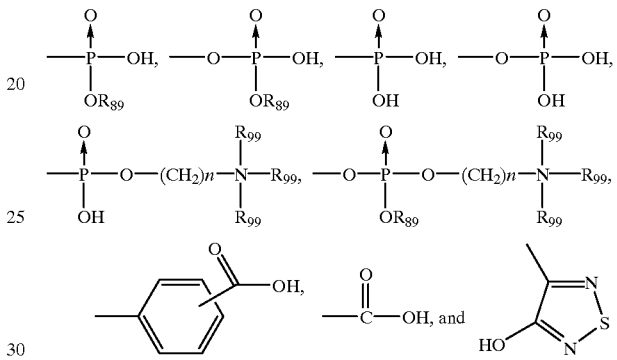

where n is from 1 to 8, $R_{89}$ is a metal or C1–C10alkyl, and $R_{99}$ is hydrogen or C1–C10 alkyl.

Preferred compounds for use in the method or composition of the invention are those having the general formula (I) or a pharmaceutically acceptable salt, solvate or prodrug derivative thereof;

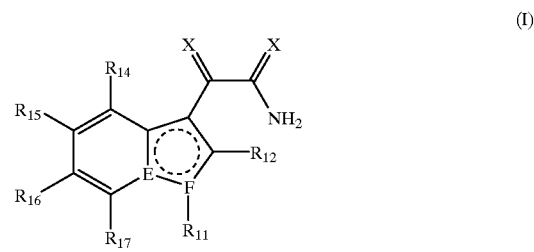

(I)

wherein;

E and F are differently C or N;

----- is presence or absence of a double bond;

each X is independently oxygen or sulfur;

$R_{11}$ is selected from groups (a), (b) and (c) where;

(a) is $C_7$–$C_{20}$ alkyl, $C_7$–$C_{20}$ alkenyl, $C_7$–$C_{20}$ alkynyl; or carbocyclic radical selected from the group cycloalkyl, cycloalkenyl, phenyl, naphthyl, norbornanyl, bicycloheptadienyl, tolyl, xylyl, indenyl, stilbenyl, terphenylyl, diphenylethylenyl, phenyl-cyclohexenyl, acenaphthyl, and anthryl, biphenylyl, bibenzylyl and related bibenzylyl homologues represented by the formula (bb),

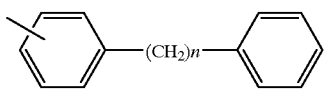

(bb)

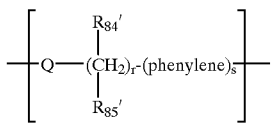

where n is a number from 1 to 8; or
(b) is a member of (a) substituted with one or more independently selected non-interfering substituents selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolyl, xylyl, biphenylyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O-($C_1$–$C_6$ alkyl), benzyloxy, phenoxy, phenylthio, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8;
(c) is the group -($L_1$)-$R_{81}$; where, -($L_1$)- is a divalent linking group having the formula;

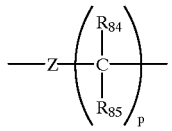

where,
$R_{84}$ and $R_{85}$ are each independently selected from hydrogen, $C_1$–$C_{10}$ alkyl, carboxy, carbalkoxy, or halo;
p is 1 to 5,
Z is a bond, —$(CH_2)$—, —O—, —N($C_1$–$C_{10}$ alkyl)-, —NH—, or —S—; and where $R_{81}$ is a group selected from (a) or (b);
$R_{12}$ is hydrogen, halo, $C_1$–$C_3$ alkyl, $C_3$–$C_4$ cycloalkyl, $C_3$–$C_4$ cycloalkenyl, —O-($C_1$–$C_2$ alkyl), or —S-($C_1$–$C_2$ alkyl);
$R_{14}$ is hydrogen or a group, -($L_a$)-(acidic group) wherein -($L_a$)- is represented by the formula;

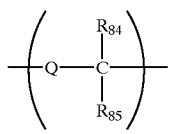

where Q is selected from the group —$(CH_2)$—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, and halo;
$R_{15}$ is hydrogen or a group, -(La')-(acidic group) wherein -(La')- is represented by the formula;

$$\left[\begin{array}{c} R_{84}' \\ | \\ Q—(CH_2)_r-(phenylene)_s \\ | \\ R_{85}' \end{array}\right]$$

where r is a number from 1 to 7, s is 0 or 1, and Q is selected from the group —$(CH_2)$—, —O—, —NH—, and —S—, and $R_{84'}$ and $R_{85'}$ are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; provided that at least one of $R_{14}$ or $R_{15}$ must be the group, -(La)-(acidic group) or -(La')-(acidic group);
$R_{16}$ is hydrogen, carboxyl or ester thereof;
$R_{17}$ is selected from hydrogen, non-interfering substituents, selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolyl, xylyl, biphenylyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O-($C_1$–$C_6$ alkyl), benzyloxy, phenoxy, phenylthio, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

A preferred class of compounds for the method or composition of the invention are compounds represented by the formula (II):

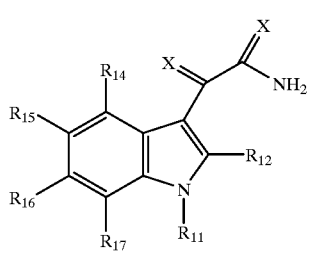

(II)

wherein X, $R_{11}$, $R_{12}$, $R_{14}$, $R_{15}$, $R_{16}$ and $R_{17}$ are as defined above.

An alternatively preferred class of compounds for the method or composition of the invention are compounds represented by the formula (III):

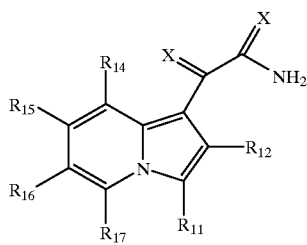

(III)

wherein X, $R_{11}$, $R_{12}$, $R_{14}$, $R_{15}$, $R_{16}$ and $R_{17}$ are as defined above.

A further preferred class of compounds for the method or composition of the invention are the compounds represented by the formula (II) or (III) where both X's are oxygen, only one of $R_{14}$ or $R_{15}$ is -($L_a$)-(acidic group) or -($L_a'$)-(acidic group), and the acidic group is carboxyl.

Specific preferred compounds and all pharmaceutically acceptable salts, solvates and prodrug derivatives thereof which are useful in the method or composition of the invention include the following:

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid,
(G) [[3-(2-Amino-1,2-dioxoethyl)-1-[(4-fluorophenyl)methyl]-2-methyl-1H-indol-4-yl]oxy]acetic acid,
(H) [[3-(2-Amino-1,2-dioxoethyl)-2-methyl-1-[(1-naphthyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl-1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (O),
(Q) [8-(Carbomethoxymethyloxy)-2-ethyl-3-(o-phenylbenzyl)indolizin-1-yl]glyoxylamide,
(R) [3-Benzyl-8-(carbethoxymethyloxy)-2-ethylindolizin-1-yl]glyoxylamide,
(S) [8-(Carbethoxymethyloxy)-2-ethyl-3-(o-phenylbenzyl)indolizin-1-yl]glyoxylamide,
(T) [3-Benzyl-8-(carbethoxymethyloxy)-2-methylindolizin-1-yl]glyoxylamide,
(U) [8-(Carbethoxymethyloxy)-3-(m-chlorobenzyl)-2-ethylindolizin-1-yl]glyoxylamide,
(V) [8-Carbethoxymethyloxy-2-ethyl-3-(1-naphthylmethyl)indolizin-1-yl]glyoxylamide,
(W) [3-Benzyl-8-(t-butoxycarbonylmethyloxy)-2-ethylindolizin-1-yl]glyoxylamide,
(X) [8-(Carbmethoxymethyloxy)-2-ethyl-3-(m-trifluoromethylbenzyl)indolizin-1-yl]glyoxylamide,
(Y) [8-(Carbmethoxymethyloxy)-2-cyclopropyl-3-(o-phenylbenzyl)indolizin-1-yl]glyoxylamide,
(Z) [3-Benzyl-8-(carboxymethyloxy)-2-ethylindolizin-1-yl]glyoxylamide,
(AA) [8-(Carboxymethyloxy)-2-ethyl-3-(o-phenylbenzyl)indolizin-1-yl]glyoxylamide,
(BB) [3-Benzyl-8-(carboxymethyloxy)-2-methylindolizin-1-yl]glyoxylamide,
(CC) [8-(Carboxymethyloxy)-3-(m-chlorobenzyl)-2-ethylindolizin-1-yl]glyoxylamide,
(DD) [8-(Carboxymethyloxy)-2-ethyl-3-(m-trifluoromethylbenzyl)indolizin-1-yl]glyoxylamide,
(EE) [8-Carboxymethyloxy-2-ethyl-3-(1-naphthylmethyl)indolizin-1-yl]glyoxylamide,
(FF) [8-(Carboxymethyloxy)-2-cyclopropyl-3-(o-phenylbenzyl)indolizin-1-yl]glyoxylamide,
(GG) mixtures of (Q) through (FF).

Most preferred in the practice of the method or composition of the invention are 1H-indole-3-glyoxylamides selected from the formula:

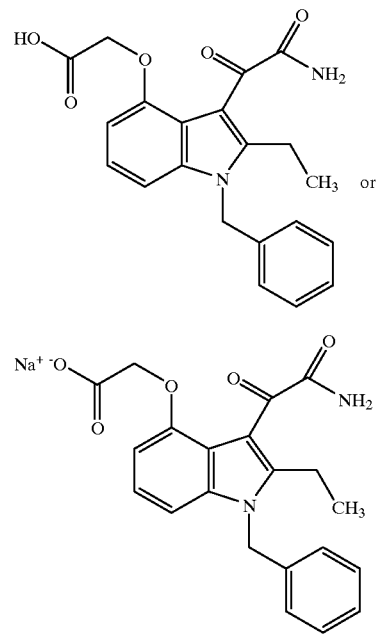

or indolizine-1-glyoxylamidles selected from the formula:

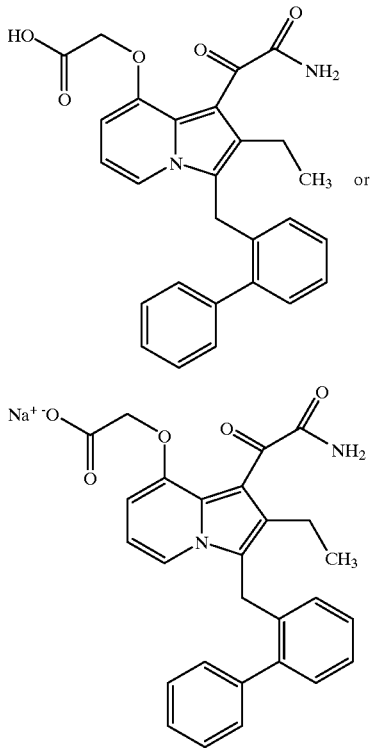

The salts of the above 1H-indole-3-glyoxylamide compounds represented by the formula (II) and named compounds (A) through (P) and of indolizine-1-glyoxylamide compounds represented by the formula (III) and named compounds (Q) through (GG) are particularly useful in the method of the invention. In those instances where the 1H-indole-3-glyoxylamide compounds and indolizine-1-glyoxylamide compounds possess acidic or basic functional groups various salts may be formed which are more water soluble and physiologically suitable than the parent compounds. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion exchange resin.

Included within the definition of pharmaceutically acceptable salts are the relatively non-toxic, inorganic and organic base addition salts of the 1H-indole-3-glyoxylamide compounds and indolizine-1-glyoxylamide compounds used in the method or composition of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," J. Phar. Sci., 66: 1–19 (1977)). Moreover, basic group(s) present in the 1H-indole-3-glyoxylamide compound may be reacted with suitable organic or inorganic acids to form salts such as acetate, benzenesulfonate, benzoate, bicarbonate, bisulfate, bitartrate, borate, bromide, camsylate, carbonate, chloride, clavulanate, citrate, chloride, edetate, edisylate, estolate, esylate, fluoride, fumarate, gluceptate, gluconate, glutamate, glycolylarsanilate, hexylresorcinate, bromide, chloride, hydroxynaphthoate, iodide, isothionate, lactate, lactobionate, laurate, malate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate.

Certain 1H-indole-3-glyoxylamide compounds and indolizine-1-glyoxylamide compounds may possess one or more chiral centers and may thus exist in optically active forms. Likewise, R- and S- isomers and mixtures thereof, including racemic mixtures as well as mixtures of cis- and transisomers, are contemplated for use by the method or composition of this invention.

Prodrugs are derivatives of the 1H-indole-3-glyoxylamide compounds or indolizine-1-glyoxylamide compounds which have chemically or metabolically cleavable groups and become by solvolysis or under physiological conditions the compounds of the invention which are pharmaceutically active in vivo. Derivatives of the 1H-indole-3-glyoxylamide compounds and indolizine-1-glyoxylamide compounds have activity in both their acid and base derivative forms, but the acid derivative form often offers advantages of solubility, tissue compatibility, or delayed release in a mammalian organism (see, Bundgard, H., Design of Prodrugs, pp. 7–9, 21–24, Elsevier, Amsterdam 1985). Prodrugs include acid derivatives well known to practitioners of the art, such as, for example, esters prepared by reaction of the parent acidic compound with a suitable alcohol, or amides prepared by reaction of the parent acid compound with a suitable amine. Simple aliphatic or aromatic esters (e.g., methyl or ethyl esters) derived from acidic groups (e.g., carboxyl) pendent on the compounds of this invention are preferred prodrugs. In some cases it is desirable to prepare double ester type prodrugs such as (acyloxy) alkyl esters or [(alkoxycarbonyl)oxy]alkyl esters.

The method of the invention can be practiced using pharmaceutical formulations containing compounds of the invention administered through the skin by an appliance such as a transdermal patch, as described in U.S. Pat. Nos. 5,296,222 and 5,271,940, the disclosures of which are incorporated herein by reference. Lipophilic prodrug derivatives of the compounds for the formula (II) are particularly well suited for transdermal absorption administration and delivery systems.

The synthesis of the 1H-indole-3-glyoxylamide compounds may be accomplished as described European Patent Application No. 95302166.4, Publication No. 0 675 110 (publ., Oct. 4, 1995). The synthesis of the indolizine compounds may be accomplished as described WO 9603383 (Publ., Feb. 8, 1996). Such synthetic methods also include well-known methods as recorded in the chemical literature and the procedure illustrated in the following preparative reaction scheme.

The following abbreviations are used throughout the synthesis Schemes and Examples.

| Et | ethyl |
| Pr | propyl |
| t-Bu | t-butyl |
| Bn | benzyl |
| LAH | lithium aluminum hydride |
| THF | tetrahydrofuran |
| DMF | dimethylformamide |

Preparative Reaction Scheme 1

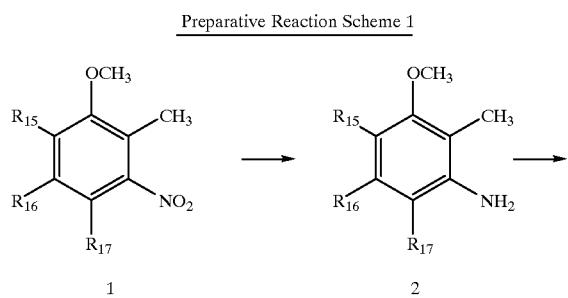

1

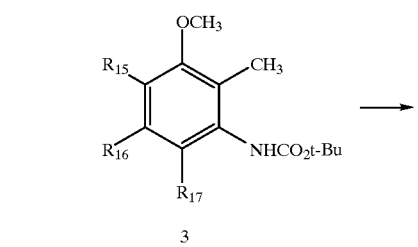

3

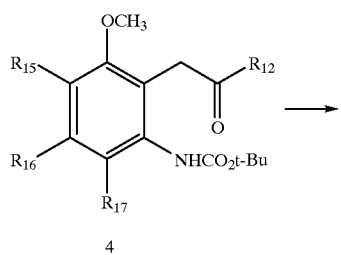

4

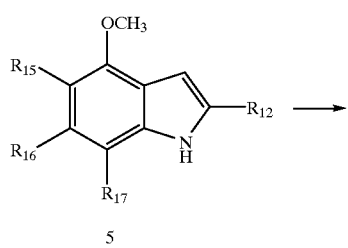

5

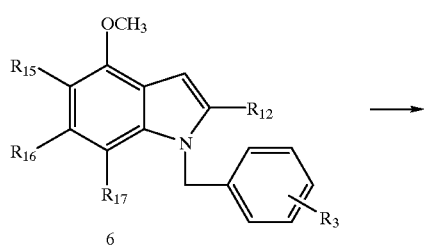

6

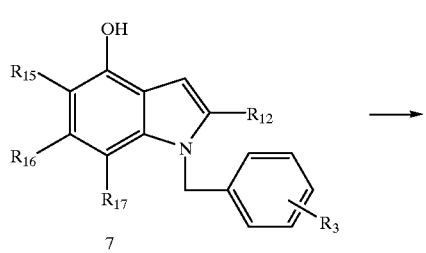

7

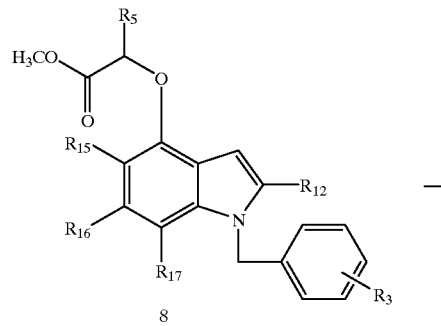

8

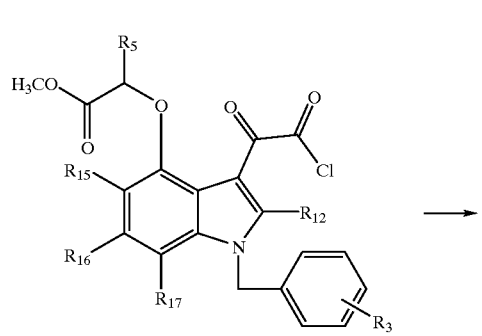

9

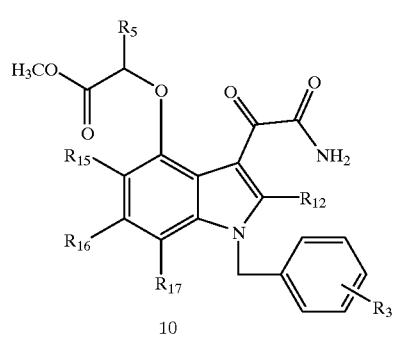

10

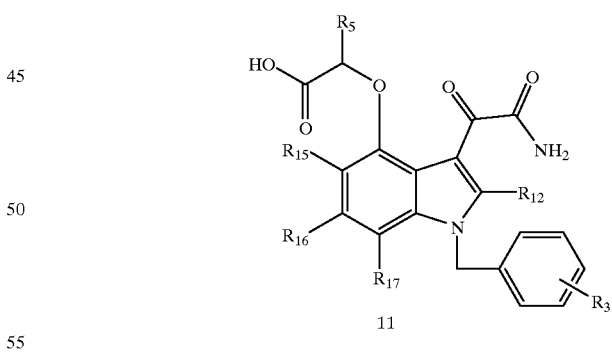

11

(wherein $R_{12}$, $R_{15}$, $R_{16}$ and $R_{17}$ are as defined above. $R_3$ is C1–C5 alkyl, aryl, C1–C6 alkoxy, halo, aryloxy, aralkyloxy, nitro, hydroxy, amino, methylamino or dimethylamino. $R_5$ is hydrogen, C1–C10 alkyl, aryl, C1–C10 alkaryl, C1–C10 aralkyl or halo.)

Explanation of Preparative Reaction Scheme 1:

To obtain the glyoxylamides substituted in the 4-position with an acidic function through an oxygen atom, the reactions outlined in scheme 1 are used (for conversions 1 through 5, see ref. Robin D. Clark, Joseph M. Muchowski, Lawrence E. Fisher, Lee A. Flippin, David B. Repke, Michel Souchet, *Synthesis*, 1991, 871–878, the disclosures of which are incorporated herein by reference). The ortho-nitrotoluene, 1, is readily reduced to the 2-methylaniline, 2, using Pd/C as catalyst. The reduction can be carried out in ethanol or tetrahydrofuran (THF) or a combination of both, using a low pressure of hydrogen. The aniline, 2, on heating with di-tert-butyl dicarbonate in THF at reflux temperature is converted to the N-tert-butylcarbonyl derivative, 3, in good yield. The dilithium salt of the dianion of 3 is generated at −40 to −20° C. in THF using sec-butyl lithium and reacted with the appropriately substituted N-methoxy-N-methylalkanamide. This product, 4, may be purified by crystallization from hexane, or reacted directly with trifluoroacetic acid in methylene chloride to give the 1,3-unsubstituted indole 5. The 1,3-unsubstituted indole 5 is reacted with sodium hydride in dimethylformamide at room temperature (20–25° C.) for 0.5–1.0 hour. The resulting sodium salt of 5 is treated with an equivalent of arylmethyl halide and the mixture stirred at a temperature range of 0–100° C., usually at ambient room temperature, for a period of 4 to 36 hours to give the 1-arylmethylindole, 6. This indole, 6, is O-demethylated by stirring with boron tribromide in methylene chloride for approximately 5 hours (see ref. Tsung-Ying Shem and Charles A Winter, Adv. Drug Res., 1977, 12, 176, the disclosure of which is incorporated herein by reference). The 4-hydroxyindole, 7, is alkylated with an alpha bromoalkanoic acid ester in dimethylformamide (DMF) using sodium hydride as a base, with reactions conditions similar to that described for the conversion of 5 to 6. The α-[(indol-4-yl)oxy]alkanoic acid ester, 8, is reacted with oxalyl chloride in methylene chloride to give 9, which is not purified but reacted directly with ammonia to give the glyoxlamide 10. This product is hydrolyzed using 1N sodium hydroxide in MeOH. The final glyoxylamide, 11, is isolated either as the free carboxylic acid or as its sodium salt or in both forms.

Preparative Reaction Scheme 2-1

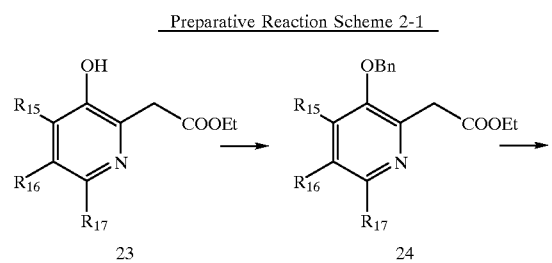

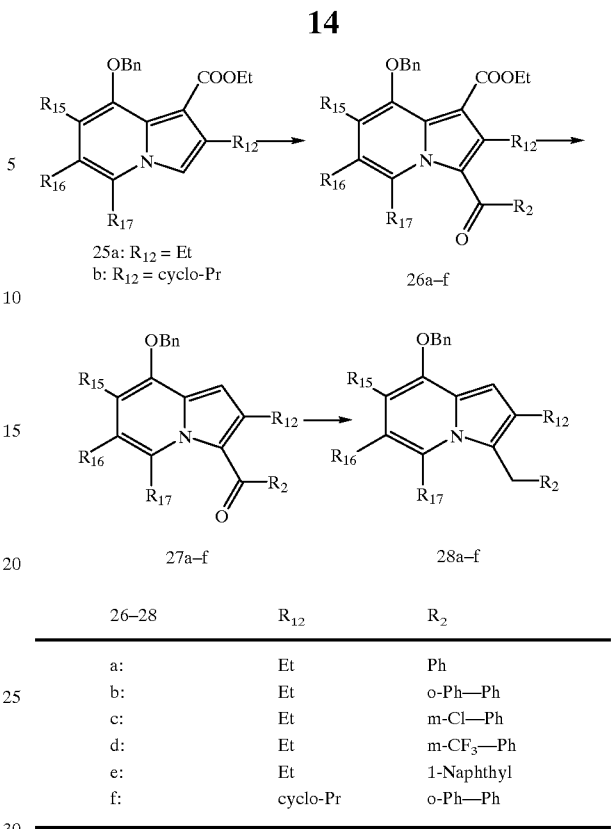

| 26–28 | $R_{12}$ | $R_2$ |
|---|---|---|
| a: | Et | Ph |
| b: | Et | o-Ph—Ph |
| c: | Et | m-Cl—Ph |
| d: | Et | m-CF$_3$—Ph |
| e: | Et | 1-Naphthyl |
| f: | cyclo-Pr | o-Ph—Ph |

(wherein $R_{12}$, $R_{15}$, $R_{16}$ and $R_{17}$ are as defined above. $R_2$ is C6–C20 alkyl, C6–C20 alkenyl, C6–C20 alkynyl or carbocyclic radical.)

Explanation of Preparative Reaction Scheme 2-1:

Compound 23 (N. Desideri F. Mama, M. L. Stein, G. Bile, W. Filippeelli, and E. Marmo, Eur. J. Med. Chem. Chim. Ther., 18, 295, (1983)) is O-alkylated using sodium hydride and benzyl chloride to give 24. N-alkylation of 24 by 1-bromo-2-butanone or chloromethylcyclopropyl ketone and subsequent base catalyzed cyclization gives 25 which is acylated by aroyl halide to give 26. Hydrolysis of the ester function of 26 followed by acidification forms an acid which is thermally decarboxylated to give 27. Reduction of the ketone function of 27 by LAH yields indolizines 28.

Preparative Reaction Scheme 2-2

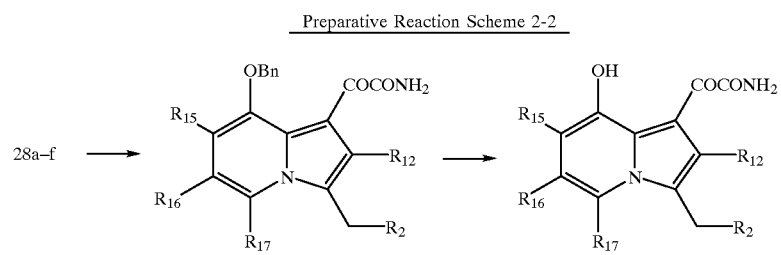

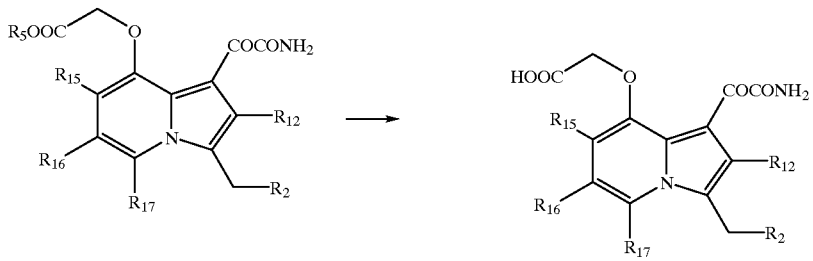

37a–d, f–k: $R_5$ = Et
38a: $R_5$ = tBu
39d, i, k, l: $R_5$ = Me

40a–d, f–l

| 35–40 | $R_3$ | $R_4$ | $R_{12}$ | $R_2$ |
|---|---|---|---|---|
| a: | H | H | Et | Ph |
| d: | H | H | Et | o-Ph—Ph |
| g: | H | H | Me | Ph |
| h: | H | H | Et | m-Cl—Ph |
| i: | H | H | Et | m-CF$_3$—Ph |
| j: | H | H | Et | 1-Naphthyl |
| k: | H | H | cyclo-Pr | o-Ph—Ph |
| l: | H | H | Me | cyclo-Hex |

(wherein $R_2$, $R_{12}$, $R_{15}$, $R_{16}$ and $R_{17}$ are as defined above. $R_5$ is hydrogen or C1–C6 alkyl.)

Explanation of Preparative Reaction Scheme 2-2:

Sequential treatment of 28 with oxalyl chloride and ammonium hydroxide forms 35 which is debenzylated by hydrogen in the presence of Pd/C to give 36. Indolizines 36 are 0-alkylated using sodium hydride and bromoacetic acid esters to form 37, 38, or 39 which are converted to indolizines 40 by hydrolysis with aqueous base followed by acidification.

Pharmaceutical Formulations

Suitable pharmaceutical formulation of the 1H-indole-3-glyoxylamide compounds may be made as described European Patent Application No. 95302166.4, Publication No. 0 675 110 (publ., Oct. 4, 1995). Suitable pharmaceutical formulation of the indolizine-1-glyoxylamide compounds may be made as described WO 9603383 (publ., Feb. 8, 1996). Formulations may be obtained by conventional procedures well known in the pharmaceutical art.

The 1H-indole-3-glyoxylamide compound or indolizine-1-glyoxylamide compound is generally administered as an appropriate pharmaceutical composition which comprises a therapeutically effective amount of 1H-indole-3-glyoxylamide compound or indolizine-1-glyoxylamide is together with a pharmaceutically acceptable diluent or carrier, the composition being adapted for the particular route of administration chosen. By "pharmaceutically acceptable" it is meant the carrier, diluent or excipient must be compatible with the 1H-indole-3-glyoxylamide compound or indolizine-1-glyoxylamide compound in the formulation and not deleterious to the subject being treated.

Preferably the pharmaceutical formulation is in unit dosage form. The unit dosage form can be a capsule or tablet itself, or the appropriate number of any of these. The quantity of active ingredient in a unit dose of composition may be varied or adjusted from about 0.1 to about 1000 milligrams or more according to the particular treatment involved.

The compound can be administered by a variety of routes including oral, aerosol, rectal, transdermal, subcutaneous, intravenous, intramuscular, and intranasal.

For the pharmaceutical formulations any suitable carrier known in the art can be used. In such a formulation, the carrier may be a solid, liquid, or mixture of a solid and a liquid. A solid carrier can be one or more substances which may also act as flavoring agents, lubricants, solubilisers, suspending agents, binders, tablet disintegrating agents and encapsulating material.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc. In tablets the 1H-indole-3-glyoxylamide compound or indolizine-1-glyoxylamide compound is mixed with a carrier having the necessary binding properties in suitable proportions and compacted in the shape and size desired. The powders and tablets preferably contain from about 1 to about 99 weight percent of the 1H-indole-3-glyoxylamide compound or indolizine-1-glyoxylamide compound.

Sterile liquid form formulations include suspensions, emulsions, syrups and elixirs. The active ingredient can be dissolved or suspended in a pharmaceutically acceptable carrier, such as sterile water, sterile organic solvent or a mixture of both.

EXAMPLES

The following Example 1 illustrates the preparation of [[3-(2-Amino-1,2-dioxoethyl)-2-ethyl-1-(phenylmethyl)-1H-indol-4-yl]oxy]acetic acid, a 1H-indole-3-glyoxylamide compound useful in the practice of the method of the invention:

Example 1

Preparation of [[3-(2-Amino-1,2-dioxoethyl)-2-ethyl-1-(phenylmethyl)-1H-indol-4-yl]oxy]acetic acid, a compound represented by the formula:

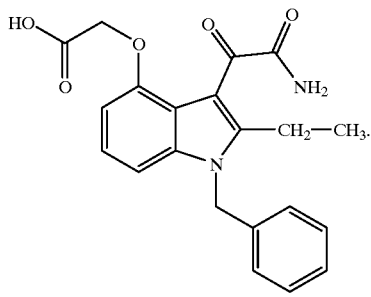

Part A. Preparation of 2-Ethyl-4-methoxy-1H-indole.

A solution of 140 mL (0.18 mol) of 1.3M sec-butyl lithium in cyclohexane was added slowly to N-tert-butoxycarbonyl-3-methoxy-2-methylaniline (21.3 g, 0.09 mol) in 250 mL of THF keeping the temperature below −40° C. with a dry ice-ethanol bath. The bath was removed and the temperature allowed to rise to 0° C. and then the bath replaced. After the temperature had cooled to −60° C., 18.5 g (0.18 mol) of N-methoxy-N-methylpropanamide in an equal volume of THF was added dropwise. The reaction mixture was stirred 5 minutes, the cooling bath removed and stirred an additional 18 hours. It was then poured into a mixture of 300 mL of ether and 400 mL of 0.5N HCl. The organic layer was separated, washed with water, brine, dried over $MgSO_4$, and concentrated at reduced pressure to give 25.5 g of a crude of 1-[2-(tert-butoxycarbonylamino)-6-methoxyphenyl]-2-butanone. This material was dissolved in 250 mL of methylene chloride and 50 mL of trifluoroacetic acid and stirred for a total of 17 hours. The mixture was concentrated at reduced pressure and ethyl acetate and water added to the remaining oil. The ethyl acetate was separated, washed with brine, dried ($MgSO_4$) and concentrated. The residue was chromatographed three times on silica eluting with 20% EtOAc/hexane to give 13.9 g of 2-ethyl-4-methoxy-1H-indole.

Analyses for $C_{11}H_{13}NO$:

Calculated: C, 75.40; H, 7.48; N, 7.99; Found: C, 74.41; H, 7.64; N, 7.97.

Part B. Preparation of 2-Ethyl-4-methoxy-1-(phenylmethyl)-1H-indole.

2-Ethyl-4-methoxy-1H-indole (4.2 g, 24 mmol) was dissolved in 30 mL of DMF and 960 mg (24 mmol) of 60% NaH/mineral oil was added. After 1.5 hours, 2.9 mL (24 mmol) of benzyl bromide was added. After 4 hours, the mixture was diluted with water and extracted twice with ethyl acetate. The combined ethyl acetate was washed with brine, dried ($MgSO_4$) and concentrated at reduced pressure. The residue was chromatographed on silica gel and eluted with 20% EtOAc/hexane to give 3.1 g (49% yield) of 2-ethyl-4-methoxy-1-(phenylmethyl) 1H-indole.

Part C. Preparation of 2-Ethyl-4-hydroxy-1-(phenylmethyl)-1H-indole.

By the method used in Example 1, Part D, in EP Publication No. 0 675 110, 3.1 g (11.7 mmol) of 2-ethyl-4-methoxy-1-(phenylmethyl)-1H-indole was O-demethylated by treating it with 48.6 mL of 1M $BBr_3/CH_2Cl_2$ to give a material that was chromatographed on silica gel (eluted with 20% EtOAc/hexane) to give 1.58 g (54% yield) of 2-ethyl-4-hydroxy-1-(phenylmethyl)-1H-indole, mp, 86–90° C.

Analyses for $C_{17}H_{17}NO$:

Calculated: C, 81.24; H, 6.82; N, 5.57; Found: C, 81.08; H, 6.92; N, 5.41.

Part D. Preparation of 2-[[2-Ethyl-1-(phenylmethyl)-1H-indol-4-yl]oxy]acetic acid methyl ester.

Using the procedure described in Example 1, Part E, in EP Publication No. 0 675 110, 2-ethyl-4-hydroxy-1-(phenylmethyl)-1H-indole (1.56 g, 6.2 mmol) was treated with 248 mg (6.2 mmol) of 60% NaH/mineral oil and then 0.6 mL (6.2 mmol) of methyl bromoacetate. The product was purified by chromatography over silica gel eluting with 20% EtOAc/hexane, to give 1.37 g (69% yield) of [[2-ethyl-1-(phenylmethyl)-1H-indol-4-yl]oxyl]acetic acid methyl ester; mp 89–92° C.

Analyses for $C_{20}H_{21}NO_3$:

Calculated: C, 74.28; H, 6.55; N, 4.33; Found: C, 74.03; H, 6.49; N, 4.60.

Part E. Preparation of [[3-(2-Amino-1,2-dioxoethyl)-2-ethyl-1-(phenylmethyl)-1H-indol-4-yl]oxy]acetic acid methyl ester.

Using the procedure in Example F, in EP Publication No. 0 675 110, 1.36 g (4.2 mmol) of [[2-ethyl-1-(phenylmethyl)-1H-indol-4-yl]oxy]acetic acid methyl ester was reacted first with 0.4 mL (4.2 mmol) of oxalyl chloride and then excess ammonia to give a white solid. This was stirred with ethyl acetate and the insoluble material separated and dried to give 1.37 g of a mixture of [[3-(2-amino-1,2-dioxoethyl)-2-ethyl-1-(phenylmethyl)-1H-indol-4-yl]oxy]acetic acid methyl ester and ammonium chloride. This mixture melted at 172–187° C.

Part F. Preparation of [[3-(2-Amino-1,2-dioxoethyl)-2-ethyl-1-(phenylmethyl)-1H-indol-4-yl]oxy]acetic acid.

A mixture of 788 mg (2 mmol) of [3-(2-Amino-1,2-dioxoethyl)-2-ethyl-1-(phenylmethyl)-1H-indol-4-yl]oxy] acetic acid methyl ester, 10 mL of 1N NaOH and 30 mL of MeOH was heated to maintain reflux for 0.5 hour, stirred at room temperature for 0.5 hour and concentrated at reduced pressure. The residue was taken up in ethyl acetate and water, the aqueous layer separated and made acidic to pH 2–3 with 1N HCl. The precipitate was filtered and washed with ethyl acetate to give 559 mg (74% yield) of [[3-(2-Amino-1,2-dioxoethyl)-2-ethyl-1-(phenylmethyl)-1H-indol-4-yl]oxy]acetic acid, mp 230–234° C.

Analyses for $C_{21}H_{20}N_2O_5$:

Calculated: C, 65.96; H, 5.80; N, 7.33; Found: C, 66.95; H, 5.55; N, 6.99.

The following Example 2 illustrates the preparation of (8-(Carbomethoxymethyloxy)-2-ethyl-3-(o-phenylbenzyl) indolizin-1-yl)glyoxylamide, a indolizine-1-glyoxylamide compound useful in the practice of the method of the invention:

Example 2

Part A: Preparation of Ethyl 3-benzyloxy-2-pyridineacetate 24

60% Sodium hydride (2.69 g, 66.2 mmol) was added in small portions to a solution of ethyl 3-hydroxy-2-pyridineacetate (23, 12.0 g, 66.2 m mol) (N. Desideri, F. Manna, M. L. Stein, G. Bile, W. Filippeelli, and E. Marmo. Eur. J. Med. Chem. Chim. Ther., 18, 295 (1983)) in dimethylformamide (220 ml) at 0° C. The mixture was stirred at 0° C. for 50 min. Benzyl chloride (8.4 ml, 72.8 mmol) was added dropwise to the mixture, which was stirred overnight. Ethyl acetate was added. The mixture was washed with 5% aqueous sodium hydrogencarbonate and water and dried over $Na_2SO_4$. After removing the solvent at reduced pressure, the residue was chromatographed on silica gel eluting with AcOEt:toluene (1:19 to 1:1) to give 16.17 g (90.0% yield) of the titled compound as an oil.

IR $\nu_{max}$ (film) 1736, 1446, 1278 $cm^{-1}$. $^1H$ NMR ($CDCl_3$) δ 1.21 (3H, t, J=7.2 Hz), 3.93 (2H, s), 4.14 (2H, q, J=7.2 Hz), 5.10 (2H, s), 7.13–7.22 (2H, m), 7.32–7.43 (5H, m), 8.16 (1H, d J=4.0, 3.0 Hz). Analyses: Calc'd for $C_{16}H_{17}NO_3$: C, 70.83; H, 6.32; N, 5.16. Found: C, 70.65; H, 6.37; N, 5.20.

Part B: Preparation of Ethyl (8-benzyloxy-2-ethylindolizin-1-yl)carboxylate 25a

A mixture of pyridine derivative (24, 15.15 g, 55.8 mmol) sodium hydrogencarbonate (23.45 g, 279 mmol) and 1-bromo-2-butanone (11.4 ml, 113 mmol) in methylethylketone (250 ml) was heated under reflux for 24 hours, washed with water and dried over $Na_2SO_4$. After removing the solvent at reduced pressure, the residue was chromatographed on silica gel eluting with AcOEt:hexane (1:19 to 1:9) to give 16.66 g, (92.0% yield) of the titled compound as an oil.

IR $v_{max}$ (film) 1690, 1227, 1092 cm$^{-1}$. $^1$H NMR (CDCl$_3$) δ 1.15 (3H, t, J=7.2 Hz), 1.26 (3H, t, J=7.5 Hz), 2.82 (2H, q, J=7.5 Hz), 4.11 (2H, q, J=7.2 Hz), 5.16 (2H, s), 6.22 (1H, d, J=7.6 Hz), 6.44 (1H, t, J=7.1 Hz), 7.07 (1H, s), 7.27–7.57 (6H, m). Analyses: Calc'd for $C_{20}H_{21}NO_3$ 0.1$H_2O$: C, 73.87; H, 6.57; N, 4.31. Found: C, 73.75; H, 6.66; N, 4.30.

Part C: Preparation of Ethyl (8-benzyloxy-2-ethyl-3-(o-phenylbenzoyl)indolizin-1-yl)carboxylate 26b A mixture of the indolizine (25, 1 eq), o-phenyl benzoyl chloride (2.0 eq) and triethylamine (5.0 eq) was heated at 90° C. (bath temp.) for 2–8 hours. Ethyl acetate was added. The mixture was washed with dilute hydrochloric acid and water and dried over $Na_2SO_4$. After removing the solvent at reduced pressure, the residue was chromatographed on silica gel eluting with AcOEt:hexane (1:2) and recrystallized. 46.0% Yield. mp, 110–112° C. (ether-hexane).

Part D: Preparation of 8-Benzyloxy-2-ethyl-3-(o-phenylbenzoyl)indolizine 27b

To a solution of the ester (26, 1.0 mmol) in dimethylsulfoxide (10 ml), 50% aqueous potassium hydroxide (3 ml) was added. The mixture was heated at 140° C. for 2–24 hours. After cooling, the mixture was acidified with dilute hydrochloric acid and extracted with ethyl acetate. The extracts were washed with water dried over $Na_2SO_4$. After removing the solvent under reduced pressure, the residue was purified by recrystallization to give the carboxylic acid. The acid in toluene was heated under reflux for 1 hour and the solvent was removed by distillation at reduced pressure. The residue was purified by recrystallization to give 27. Quantitative yield.

IR $v_{max}$ (nujol) 1735, 1597, 742 cm$^{-1}$.

Part E: Preparation of 8-Benzyloxy-2-ethyl-3-(o-phenylbenzyl)indolizine 28b

Compound 27 was treated by the procedure described for the preparation of 4, WO 9603383. Quantitative yield.

IR $v_{max}$ (CHCl$_3$) 1525, 1259 cm$^{-1}$.

Part F: Preparation of (8-Benzyloxy-2-ethyl-3-(o-phenylbenzyl)indolizin-1-yl)glyoxylamide 35d These compounds were prepared according to the procedure described for the synthesis of compound 8 from compound 4, WO 9603383. 79.0% Yield.

mp, 183–185° C. (ether-hexane).

Part G: Preparation of (2-Ethyl-8-hydroxy-3-(o-phenylbenzyl)indolizin-1-yl)glyoxylamide 36d These compounds were prepared according to the procedure described for the synthesis of compound 20 from 19, WO 9603383. 95.0% Yield.

mp, 195–196° C. (dec.) (ether-hexane).

Part H: Preparation of (8-(Carbomethoxymethyloxy)-2-ethyl-3-(o-phenylbenzyl)indolizin-1-yl)glyoxylamide 39d These compounds were prepared according to the procedure described for the synthesis of compound 21 from 20, WO 9603383. 84% Yield.

mp, 73–75° C. (dec.) (ether-hexane).

Part I: Preparation of (8-(Carboxymethyloxy)-2-ethyl-3-(o-phenylbenzyl)indolizin-1-yl)glyoxylamide 40d 1N-Aqueous potassium hydroxide (4 ml) was added to a solution of the ester (37–39, 2 mmol) in methanol (21 ml). The solution was stirred at room temperature for 40 min, washed with ether, acidified with 2N-HCl and extracted with ethyl acetate. The extracts were washed with water and dried over $Na_2SO_4$. After removing the solvent at reduced pressure, the residue was recrystallized. 93% Yield.

mp, 209–212° C. (dec.) (ether-hexane). IR $v_{max}$ (nujol) 3316, 1704, 1601, 1493 cm$^{-1}$. $^1$H NMR (d$_6$-DMSO) δ 1.01 (3H, t, J=7.5 Hz), 2.67 (2H, q, J=7.5 Hz), 4.18 (2H, s), 4.71 (2H, s), 6.41 (1H, d, J=7.8 Hz), 6.57–6.59 (2H, m), 7.14–7.57 (10H, m), 7.34 (1H, s), 13.09 (1H, br.s). Analyses: Calc'd for $C_{27}H_{24}N_2O_5$.0.3$H_2O$: C, 70.21; H, 5.37; N, 6.06. Found: C, 70.17; H, 5.35; N, 5.98.

The stroke treatment utility of the method of the invention will now be illustrated by the following Example 3 and 4:

Example 3

This example illustrates the effect of [[3-(2-Amino-1,2-dioxoethyl)-2-ethyl-1-(phenylmethyl)-1H-indol-4-yl]oxy] acetic acid (the compound prepared by Example 1, hereinafter called "Ex-1") on cerebral infarction in a rat focal stroke model.

Experimental protocol:

Wistar male rats weighing 240–260 g were used. The body temperature of the animals was maintained at 37.5° C. with a heating pad during the operation. Anesthesia was induced with 3% halothane in 30% oxygen and maintained with 1–1.5% halothane in 30% oxygen. A catheter for the administration of rose bengal and Ex-1 was placed in the femoral vein. A subtemporal craniotomy was performed using a dental drill under an operating microscope to open a 3-mm diameter circular bone window, through which photo-irradiation with green light (wave length, 540 nm) was achieved by using a xenon lamp (Umemura et al. *Stroke* 24, 1077–1082, 1993). The head of optic fiber with 3-mm-diameter was placed on the window in the skull base, and rose bengal (20 mg/kg) was injected intravenously. Photo-irradiation on the main trunk of left middle cerebral artery (MCA) was performed for 10 minutes. The incisions were closed after the confirmation of thrombotic occlusion. Twenty-four hours after the completion of the irradiation, cerebrum was removed under pentobarbital (50 mg/kg i.p.) anesthesia. The cerebrum was coronally sectioned in 1-mm thicknesses from the frontal lobe with a microslicer, and then consecutive slices were stained with triphenyltetrazolium chloride (TTC). Photographs of the slices were taken. The infarction volumes of cerebral cortex and striatum were determined by the integration of the surfaces of sections and distances between them. Ex-1, dissolved in 0.9% saline, was injected as a bolus (3 mg/kg, i.v.) 5 minutes or 2 hours after occlusion of the MCA and then infused (0.5 mg/kg/hr, i.v.) until 24 hours after the MCA occlusion. Data are expressed as ±S.D. Statistical analysis was performed with unpaired Student's t test or Dunnett's t test. A value of P<0.05 was considered significant.

TABLE 1

(Ex-1 compound activity)

| PIT-MCAO | | | Ex-1 (3 mg/kg i.v. + 0.5 mg/kg/hr i.v.) | | | |
|---|---|---|---|---|---|---|
| Infarct volume | Control | | Post-5 min | | Post-2 hr | |
| (mm3) | Cortex | Striatum | Cortex | Striatum | Cortex | Striatum |
| Rat No. R1 | 146.2 | 63.0 | 91.3 | 92.1 | 90.6 | 57.2 |
| R2 | 145.2 | 89.3 | 98.6 | 84.6 | 81.2 | 46.0 |
| R3 | 168.1 | 84.2 | 108.8 | 71.0 | 88.0 | 69.1 |
| R4 | 123.0 | 71.6 | 137.7 | 82.4 | 101.3 | 50.8 |
| R5 | 172.3 | 103.7 | 78.7 | 66.2 | 113.3 | 61.5 |
| R6 | 113.8 | 80.1 | 66.0 | 40.4 | 111.2 | 73.8 |
| R7 | 138.2 | 68.7 | 98.4 | 65.5 | | |
| R8 | 168.4 | 74.7 | | | | |
| Mean | 146.9 | 79.4 | 97.1 | 71.7 | 97.6 | 59.7 |
| S.D. | 21.7 | 13.0 | 22.8 | 17.1 | 13.1 | 10.6 |
| t-Test vs. Cont. | | | P < 0.01 | None | P < 0.01 | P < 0.01 |

Note: PIT-MCAO is photochemically induced thrombosis-middle cerebal artery occlusion.

Results:

As shown by the test results in Table 1 compound Ex-1 (3 mg/kg i.v.+0.5 mg/kg/hr i.v. until 24 hours after the MCA occlusion) significantly reduced cerebral infarction size, which was observed not only at 5 minutes post-treatment but also at 2 hours post-treatment.

Example 4

This example illustrates the effect of (8-(Carbomethoxymethyloxy)-2-ethyl-3-(o-phenylbenzyl)indolizin-1-yl)glyoxylamide (the compound prepared by Example 2, hereinafter called "Ex-2") on cerebral infarction in a rat focal stroke model The experiment was carried out in the same method as in Example 3 mentioned above other than the following.

Ex-2 (10 or 30 mg/kg, p.o.) was suspended on 0.6% arabic gum solution and administered 1 hour before or 2 hours after the MCA occlusion.

TABLE 2

(Ex-2 compound activity)

| PIT-MCAO | | Ex-2 (p.o.; Post 2 hr) | |
|---|---|---|---|
| Infarct volume (mm3) | Control Cortex | 10 mg/kg Cortex | 30 mg/kg Cortex |
| Rat No. R1 | 159.3 | 124.9 | 100.3 |
| R2 | 154.9 | 91.0 | 129.5 |
| R3 | 136.6 | 80.6 | 62.9 |
| R4 | 118.5 | 112.0 | 99.9 |
| R5 | 122.2 | 96.9 | 67.1 |
| R6 | 161.3 | 84.8 | 88.8 |
| Mean | 142.1 | 98.4 | 91.4 |
| S.D. | 19.0 | 17.0 | 24.5 |
| t-Test vs. Cont. | | P < 0.01 | P < 0.01 |

| PIT-MCAO Infarct volume (mm3) | Control Cortex | Ex-2 (p.o.; Pre 1 hr) 30 mg/kg Cortex |
|---|---|---|
| Rat No. R1 | 104.2 | 105.4 |
| R2 | 119.1 | 83.2 |
| R3 | 127.5 | 77.9 |
| R4 | 166.8 | 76.0 |
| R5 | 85.8 | 109.3 |
| R6 | 100.7 | 68.0 |
| Mean | 117.4 | 86.6 |
| S.D. | 28.3 | 16.8 |
| t-Test vs. Cont. | | P < 0.05 |

Result:

As shown by the test results in Table 2 compound Ex-2 (10 or 30 mg/kg, p.o. an orally available indolizine derivative), also significantly reduced cerebral infarct size regardless of the treatment at 1 hour before or at 2 hours after the MCA occlusion.

The following pharmaceutical formulations 1 through 8 are illustrative only and are not intended to limit the scope of the invention in any way. "Active ingredient", refers to a compound according to formula (I) or a pharmaceutically acceptable salt, solvate, or prodrug thereof.

Formulation 1

Hard gelatin capsules are prepared using the following ingredients:

| | Quantity (mg/capsule) |
|---|---|
| Active ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active ingredient | 250 |
| Cellulose, microcrystalline | 400 |
| Silicon dioxide, fumed | 10 |
| Stearic acid | 5 |
| Total | 665 |

Formulation 3

An aerosol solution is prepared containing the following components:

| | Weight |
|---|---|
| Active ingredient | 0.25 |
| Ethanol | 25.75 |
| Propellant 22 | 74.00 |
| (Chlorodifluoromethane) | |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are then fitted to the container.

Formulation 4

Tablets, each containing 60 mg of active ingredient, are made as follows:

| | |
|---|---|
| Active ingredient | 60 mg |
| Starch | 45 mg |
| Microcrystalline cellulose | 35 mg |
| Polyvinylpyrrolidone | 4 mg |
| (as 10% solution in water) | |
| Sodium carboxymethyl starch | 4.5 mg |
| Magnesium stearate | 0.5 mg |
| Talc | 1 mg |
| Total | 150 mg |

The active ingredient, starch and cellulose are passed through a No.45 mesh U.S.sieve and the mixed thoroughly. The aqueous solution containing polyvinylpyrrolidone is mixed with the resultant powder, and the mixture then is passed through a No.14 mesh U.S.sieve. The granules so produced are dried at 50° C. and passed through No.18 mesh U.S.sieve. The sodium carboxymethyl starch, magnesium stearate and talc, previously passed through a No.60 mesh U.S.sieve, are then added to the granules which, after mixing, are compressed on a tablet machine to yield tablets each weighing 150 mg.

Formulation 5

Capsules, each containing 80 mg of active ingredient, are made as follows:

| | |
|---|---|
| Active ingredient | 80 mg |
| Starch | 59 mg |
| Microcrystalline cellulose | 59 mg |
| Magnesium stearate | 2 mg |
| Total | 200 mg |

The active ingredient, cellulose, and magnesium stearate are blended, passed through a No.45 mesh U.S.sieve, and filed into hard gelatin capsules in 200 mg quantities.

Formulation 6

Suppositories, each containing 225 mg of active ingredient, are made as follows:

| | |
|---|---|
| Active ingredient | 225 mg |
| Saturated fatty acid glycerides | 2000 mg |
| Total | 2225 mg |

The active ingredient is passed through a No.60 mesh U.S.sieve and suspended in the saturated fatty acid glycerides previously melted using the minimum heat necessary. The mixture is then poured into a suppository mold of nominal 2 g capacity and allowed to cool.

Formulation 7

Suspensions, each containing 50 mg of active ingredient per 5 ml dose, are made as follows:

| | |
|---|---|
| Active ingredient | 50 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No.45 mesh U.S.sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 8

| | |
|---|---|
| Active ingredient | 100 mg |
| Isotonic saline | 1000 ml |

The solution of the above ingredients generally is administered intravenously to a subject at a rate of 1 ml per minute.

While the present invention has been illustrated above by certain specific embodiments, it is not intended that these specific examples should limit the scope of the invention as described in the appended claims.

What is claimed is:

1. A method of treatment of a mammal currently afflicted with a stroke or previously afflicted with a stroke, said method comprising administering to said mammal a therapeutically effective amount of an N-heterocyclic glyoxylamide compound represented by the formula (I) or a pharmaceutically acceptable salt, solvate, or prodrug derivative thereof:

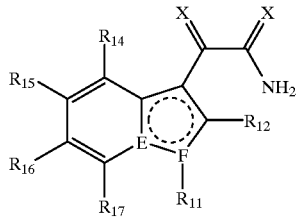

(I)

wherein;

E and F are differently C or N;

----- is presence or absence of a double bond;

each X is independently oxygen or sulfur;

$R_{11}$ is selected from groups (a), (b) and (c) where;

(a) is $C_7$–$C_{20}$ alkyl, $C_7$–$C_{20}$ alkenyl, $C_7$–$C_{20}$ alkynyl; or carbocyclic radical selected from the group cycloalkyl, cycloalkenyl, phenyl, naphthyl, norbornanyl, bicycloheptadienyl, tolyl, xylyl, indenyl, stilbenyl, terphenylyl, diphenylethylenyl, phenyl-cyclohexenyl, acenaphthyl, and anthryl, biphenylyl, bibenzylyl and related bibenzylyl homologues represented by the formula (bb),

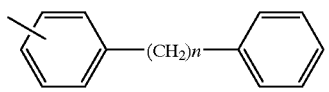

(bb)

where n is a number from 1 to 8; or (b) is a member of (a) substituted with one or more independently selected non-interfering substituents selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolyl, xylyl, biphenylyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_1$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O-($C_1$–$C_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and $C_1$–$C_6$ carbonyl; where n is from 1 to 8;

(c) is the group -(L$_1$)-R$_{81}$; where, -(L$_1$)- is a divalent linking group having the formula;

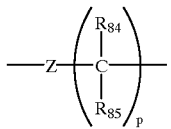

where, $R_{84}$ and $R_{85}$ are each independently selected from hydrogen, $C_1$–$C_{10}$ alkyl, carbolxy, carbalkoxy, or halo;

p is 1 to 5,

Z is a bond, —(CH$_2$)—, —O—, —N($C_1$–$C_{10}$ alkyl)-, —NH—, or —S—; and where $R_{81}$ is a group selected from (a) or (b);

$R_{12}$ is hydrogen, halo, $C_1$–$C_3$ alkyl, $C_3$–$C_4$ cycloalkyl, $C_3$–$C_4$ cycloalkenyl, —O-($C_1$–$C_2$ alkyl), or —S-($C_1$–$C_2$ alkyl);

$R_{14}$ is hydrogen or a group, -(L$_a$)-(acidic group) wherein -(L$_a$)- is represented by the formula;

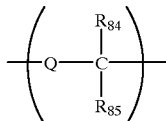

where Q is selected from the group —(CH$_2$)—, —O—, —NH—, and —S—, and $R_{84}$ and $R_{85}$ are each independently selected from hydrogen, $C_1$–$C_{10}$ alkyl, aryl, $C_1$–$C_{10}$ alkaryl, $C_1$–$C_{10}$ aralkyl, and halo;

$R_{15}$ is hydrogen or a group, -(La')-(acidic group) wherein -(La')- is represented by the formula;

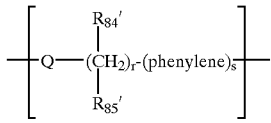

where r is a number from 1 to 7, s is 0 or 1, and Q is selected from the group —(CH$_2$)—, —O—, —NH—, and —S—, and $R_{84}$' and $R_{85}$' are each independently selected from hydrogen, $C_1$–$C_{10}$ alkyl, aryl, $C_1$–$C_{10}$ alkaryl, $C_1$–$C_{10}$ aralkyl, carboxy, carbalkoxy, and halo; provided that at least one of $R_{14}$ or $R_{15}$ must be the group, -(La)-(acidic group) or -(La')-(acidic group);

$R_{16}$ is hydrogen, carboxyl or ester thereof;

$R_{17}$ is selected from hydrogen, non-interfering substituents, selected from the group consisting of $C_1$–$C_6$ alkyl, $C_2$–$C_6$ alkenyl, $C_2$–$C_6$ alkynyl, $C_7$–$C_{12}$ aralkyl, $C_7$–$C_{12}$ alkaryl, $C_3$–$C_8$ cycloalkyl, $C_3$–$C_8$ cycloalkenyl, phenyl, tolyl, xylyl, biphenylyl, $C_1$–$C_6$ alkoxy, $C_2$–$C_6$ alkenyloxy, $C_2$–$C_6$ alkynyloxy, $C_2$–$C_{12}$ alkoxyalkyl, $C_2$–$C_{12}$ alkoxyalkyloxy, $C_2$–$C_{12}$ alkylcarbonyl, $C_2$–$C_{12}$ alkylcarbonylamino, $C_2$–$C_{12}$ alkoxyamino, $C_2$–$C_{12}$ alkoxyaminocarbonyl, $C_2$–$C_{12}$ alkylamino, $C_1$–$C_6$ alkylthio, $C_2$–$C_{12}$ alkylthiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —(CH$_2$)$_n$—O-($C_1$–$C_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8.

2. A method of treatment of a mammal currently afflicted with a stroke or previously afflicted with a stroke, said method comprising administering to said mammal a therapeutically effective amount of a 1H-indole-3-glyoxylamide compound represented by the formula (II) or a pharmaceutically acceptable salt, solvate, or prodrug derivative thereof:

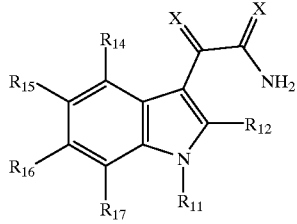
(II)

wherein each X is independently oxygen or sulfur,
R$_{11}$ is selected from groups (a), (b) and (c) where
(a) is C$_7$–C$_{20}$ all C$_7$–C$_{20}$ alkenyl, C$_7$–C$_{20}$ alkynyl; or carbocyclic radical selected from the group consisting of cycloalkyl, cycloalkenyl, phenyl, naphthyl, norbornanyl, bicycloheptadienyl, tolyl, xylyl, indenyl, stilbenyl, terphenylyl, diphenylethylenyl, phenyl-cyclohexanyl, acenaphthyl, anthryl, biphenylyl, bibenzylyl and related bibenzylyl homologues represented by the formula (bb):

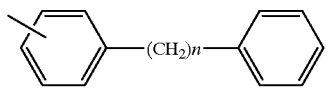
(bb)

where n is a number from 1 to 8;
(b) is a member of (a) substituted with one or more independently selected non-interfering substituents selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ alkaryl, C$_3$–C$_8$ cycloky, C$_3$–C$_8$ cycloalkenyl, phenyl, tolyl, xylyl, biphenylyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$, haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), —(CH$_2$)$_n$—O-(C$_1$–C$_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8; and
(c) is the group -(L$_1$)-R$_{81}$; where -(L$_1$)- is a divalent linking group having the formula:

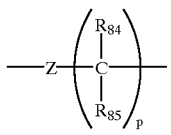

where,
R$_{84}$ and R$_{85}$ are each independently selected from the group consisting of hydrogen, C$_1$–C$_{10}$ alkyl, carboxy, carbalkoxy, and halo;
p is 1 to 5,
Z is a bond, —(CH$_2$)—, —O—, —N(C$_1$–C$_{10}$ alkyl)-, —NH—, or —S—; and where R$_{81}$ is a group selected from (a) or (b);
R$_{12}$ is hydrogen, halo, C$_1$–C$_3$ alkyl, C$_3$–C$_4$ cycloalkyl, C$_3$–C$_4$ cycloalkenyl, —O-(C$_1$–C$_2$ alkyl), or —S-(C$_1$–C$_2$ alkyl);
R$_{14}$ is hydrogen or a group, -(L$_a$)-(acidic group) wherein -(L$_a$)- is represented by the formula;

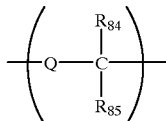

where Q is selected from the group —(CH$_2$)—, —O—, —NH—, and —S—, and R$_{84}$ and R$_{85}$ are each independently selected from the group consisting of hydrogen, C$_1$–C$_{10}$ alkyl, aryl, C$_1$–C$_{10}$ alkaryl, C$_1$–C$_{10}$ aralkyl, and halo;
R$_{15}$ is a hydrogen or a group, -(La')-(acidic group) wherein -(La)- is represented by the formula;

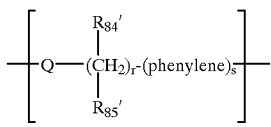

where r is a number from 1 to 7, s is 0 or 1, and Q is selected from the group consisting of —(CH$_2$)—, —O—, —NH—, and —S—, and R$_{84}$' and R$_{85}$' are each independently selected from the group consisting of hydrogen, C$_1$–C$_{10}$ alkyl, aryl, C$_1$–C$_{10}$ alkaryl, C$_1$–C$_{10}$ aralkyl, carboxy, carbalkoxy, and halo; provided that at least one of R$_{14}$ or R$_{15}$ must be the group, -(La)-(acidic group) or -(La')-(acidic roup);
R$_{16}$ is hydrogen, carboxyl or ester thereof; and
R$_{17}$ is hydrogen or a non-interfering substituent selected from the group consisting of C$_1$–C$_6$ alkyl, C$_2$–C$_6$ alkenyl, C$_2$–C$_6$ alkynyl, C$_7$–C$_{12}$ aralkyl, C$_7$–C$_{12}$ akaryl, C$_3$–C$_8$ cycloalkyl, C$_3$–C$_8$ cycloalkenyl, phenyl, tolyl, xylyl, biphenylyl, C$_1$–C$_6$ alkoxy, C$_2$–C$_6$ alkenyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbollyl, C$_2$–C$_{12}$ alkylcarbonylamino, C$_2$–C$_{12}$ alkoxyamino, C$_2$–C$_{12}$ alkoxyaminocarbonyl C$_2$–C$_{12}$ alkylamino, C$_1$–C$_6$ alkylthio, C$_2$–C$_{12}$ alkylthiocarbonyl, C$_1$–C$_6$ alkylsulflnyl, C$_1$–C$_6$ alkylsulfonyl, C$_2$–C$_6$ haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), —(CH$_2$)$_n$—O-(C$_1$–C$_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8.

3. A method of treatment of a mammal currently afflicted with a stroke or previously afflicted with a stroke, said method comprising administering to said mammal a therapeutically effective amount of an indolizine-1-glyoxylamide compound represented by the formula (III) or a pharmaceutically acceptable salt, solvate, or prodrug derivative thereof:

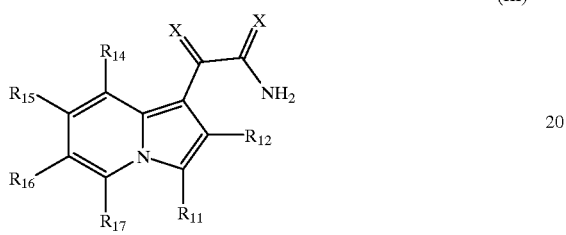

(III)

wherein each X is independently oxygen or sulfur:

R$_{11}$ is selected from groups (a), (b) and (c) where
(a) is C$_7$–C$_{20}$ alkyl, C$_7$–C$_{20}$ alkenyl, C$_7$–C$_{20}$ alkynyl; or carbocyclic radical selected from the group consisting of cycloalkyl, cycloalkenyl phenyl, naphthyl norbornanyl, bicycloheptadienyl, tolyl xylyl, indenyl, stilbenyl, terphenylyl, diphenylethylanyl, phenyl-cyclohexenyl, acenaphthyl, anthryl, biphenylyl, bibenzylyl and related bibenzylyl homologues represented by the formula (bb),

(bb)

where n is a number from 1 to 8;
(b) is a member of (a) substituted with one or more independently selected non-interfering substituents selected from the group consisting of C$_1$–C$_6$ alkyl C$_2$–C$_6$ alkenyl, C$_2$–C$_6$ alkynyl C$_7$–C$_{12}$ aralkyl, C$_7$–C$_{12}$ alkaryl C$_3$–C$_8$ cycloalkyl, C$_3$–C$_8$ cycloalkenlyl, phenlyl tolyl, xylyl, biphenlylyl, C$_1$–C$_6$ alkoxy, C$_2$–C$_6$ alkenlyloxy, C$_2$–C$_6$ alkynyloxy, C$_2$–C$_{12}$ alkoxyalkyl, C$_2$–C$_{12}$ alkoxyalkyloxy, C$_2$–C$_{12}$ alkylcarbonyl, C$_2$–C$_{12}$ alkylcarbonylamino, C$_2$–C$_{12}$ alkoxyamino, C$_2$–C$_{12}$ alkoxyaminocarbonyl, C$_1$–C$_{12}$ alkylamino, C$_1$–C$_6$ alkylthio, C$_2$–C$_{12}$ alkylthiocarbonyl, C$_1$–C$_6$ alkylsulfinyl, C$_1$–C$_6$ alkylsulfonyl, C$_2$–C$_6$ haloalkoxy, C$_1$–C$_6$ haloalkylsulfonyl, C$_2$–C$_6$ haloalkyl, C$_1$–C$_6$ hydroxyalkyl, —C(O)O(C$_1$–C$_6$ alkyl), —(CH$_2$)$_n$—O-(C$_1$–C$_6$ alkyl), benzyloxy, phenoxy, phenylthio, —CHO, amino, amidino, bromo, carbamyl, carboxyl, carbalkoxy, —(CH$_2$)$_n$—CO$_2$H, chloro, cyano, cyanoguanidinyl, fluoro, guanidino, hydrazide, hydrazino, hydrazido, hydroxy, hydroxyamino, iodo, nitro, phosphono, —SO$_3$H, thioacetal, thiocarbonyl, and C$_1$–C$_6$ carbonyl; where n is from 1 to 8; and (c) is the group -(L$_1$)-R$_{81}$; where, -(L$_1$)- is a divalent linking group having the formula;

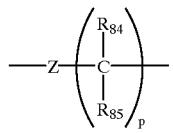

where,
R$_{84}$ and R$_{85}$ are each independently selected from the group consisting of hydrogen, C$_1$–C$_{10}$ alkyl, carboxy, carbalkoxy, or halo;
p is 1 to 5,
Z is a bond, —(CH$_2$)—, —O—, —N(C$_1$–C$_{10}$ alkyl)-, —NH—, or —S—; and where R$_{81}$ is a group selected from (a) or (b);
R$_{12}$ is hydrogen, halo, C$_1$–C$_3$ alkyl, C$_3$–C$_4$ cycloalkyl, C$_3$–C$_4$ cycloalkenyl, —O-(C$_1$–C$_2$ alkyl), or —S-(C$_1$–C$_2$ alkyl);
R$_{14}$ is hydrogen or a group, -(La)-(acidic group) wherein -(La)- is represented by the formula;

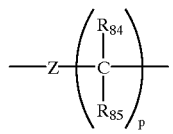

where Q is selected from the group —(CH$_2$)—, —O—, —NH—, and —S—, and R$_{84}$ and R$_{85}$ are each independently selected from the group consisting of hydrogen, C$_1$–C$_{10}$ alkyl, aryl, C$_1$–C$_{10}$ alkaryl, C$_1$–C$_{10}$ aralkyl, and halo;
R$_{15}$ is hydrogen or a group, -(La')-(acidic group) wherein -(La')- is represented by the formula;

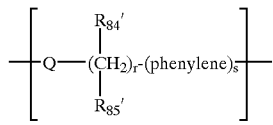

where r is a number from 1 to 7, s is 0 or 1, and Q is selected from the group consisting of —(CH$_2$)—, —O—, —NH—, and —S—, and R$_{84}$' and R$_{85}$' are each independently selected from hydrogen, C$_1$–C$_{10}$ alkyl, aryl, C$_1$–C$_{10}$ alkaryl, C$_1$–C$_{10}$ aralkyl, carboxy, carbalkoxy, and halo; provided that at least one of R$_{14}$ or R$_{15}$ must be the group, -(La)-(acidic group) or -(La')-(acidic group);
R$_{16}$ is hydrogen, carboxyl or ester thereof; and
R$_{17}$ is hydrogen or a non-interfering substituent selected from the group consisting of C$_1$–C$_6$ alkyl, C$_2$–C$_6$ alkenayl, C$_2$–C$_6$ alkynyl, C$_7$–C$_{12}$ aralkyl, C$_7$–C$_{12}$ alkaryl, C$_3$–C$_8$ cycloalkyl, C$_3$–C$_8$ cycloalkenyl, phenyl, tolyl, xylyl, biphenlylyl, C$_1$–C$_6$ alkoxy, C$_2$–C$_6$ alkenyloxy, C$_2$–C$_6$ alkynyloxy, C$_2$–C$_{12}$ alkoxcyalkyl, C$_2$–C$_{12}$ alkoxyalkyloxy, C$_2$–C$_{12}$ alkylcarbonyl, C$_2$–C$_{12}$ alkylcarbonaylamino, C$_2$–C$_{12}$ alkoxyamino, C$_2$–C$_{12}$ alkoxyaminocarbonyl, C$_2$–C$_{12}$ alkylamino, $C_1$–$C_6$ alkylthio, $C_2$–$C_{12}$ alkythiocarbonyl, $C_1$–$C_6$ alkylsulfinyl, $C_1$–$C_6$ alkylsulfonyl, $C_2$–$C_6$ haloalkoxy, $C_1$–$C_6$ haloalkylsulfonyl, $C_2$–$C_6$ haloalkyl, $C_1$–$C_6$ hydroxyalkyl, —C(O)O($C_1$–$C_6$ alkyl), —$(CH_2)_n$—O-($C_1$–$C_6$ alkyl), benzyloxy, phenoxy, phenylthio, —CHO, amino, amidino, bromo, carbamyl, carboxyl, carbalkoxy, —$(CH_2)_n$—$CO_2H$, chloro, cyano, cyanoguanidinyl, fluoro, guanidino, hydrazide, hydrazino, hydrazido, hydroxy, hydroxyamino, iodo, nitro, phosphono, —$SO_3H$, thioacetal, thiocarbonyl, and $C_1$–$C_6$ carbonyl; where n is from 1 to 8.

4. The method of claim 2 wherein for the compound of formula (II) both X are oxygen, only one of $R_{14}$ or $R_{15}$ are -(La)-(acidic group) or -(La')-(acidic group) and the (acidic group) is carboxyl.

5. A method of treatment of a mammal currently afflicted with a stroke or previously afflicted with a stroke, said method comprising administering to said mammal in need of such treatment a therapeutically effective amount of an N-heterocyclic glyoxylamide compound or a pharmaceutically acceptable salt, solvate, or a prodrug derivative thereof selected from the group consisting of compounds (A) through (GG):

(A) [[3-(2-Amino-1,2-dioxoethyl)-2-methyl-1-(phenylmethyl)-1H-indol-4-yl]oxy]acetic acid,
(B) dl-2-[[3-(2-Amino-1,2-dioxoethyl)-2-methyl-1-(phenylmethyl)-1H-indol-4-yl]oxy]propanoic acid,
(C) [[3-(2-Amino-1,2-dioxoethyl)-1-([1,1'-biphenyl]-2-ylmethyl)-2-methyl-1H-indol-4-yl]oxy]acetic acid,
(D) [[3-(2-Amino-1,2-dioxoethyl)-1-([1,1'-biphenyl]-3-ylmethyl)-2-methyl-1H-indol-4-yl]oxy]acetic acid,
(E) [[3-(2-Amino-1,2-dioxoethyl)-1-([1,1'-biphenyl]-4-ylmethyl)-2-methyl-1H-indol-4-yl]oxy]acetic acid,
(F) [[3-(2-Amino-1,2-dioxoethyl)-1-[(2,6-dichlorophenyl)methyl]-2-methyl-1H-indol-4-yl]oxy]acetic acid,
(G) [[3-(2-Amino-1,2-dioxoethyl)-1-[(4-fluorophenyl)methyl]-2-methyl-1H-indol-4-yl]oxy]acetic acid,
(H) [[3-(2-Amino-1,2-dioxoethyl)-2-methyl-1-[(1-naphthalenyl)methyl]-1H-indol-4-yl]oxy]acetic acid,
(I) [[3-(2-Amino-1,2-dioxoethyl)-2-ethyl-1-(phenylmethyl)-1H-indol-4-yl]oxy]acetic acid,
(J) [[3-(2-Amino-1,2-dioxoethyl)-1-[(3-chlorophenyl)methyl]-2-ethyl-1H-indol-4-yl]oxy]acetic acid,
(K) [[3-(2-Amino-1,2-dioxoethyl)-1-([1,1'-biphenyl]-2-ylmethyl)-2-ethyl-1H-indol-4-yl]oxy]acetic acid,
(L) [[3-(2-amino-1,2-dioxoethyl)-1-([1,1'-biphenyl]-2-ylmethyl)-2-propyl-1H-indol-4-yl]oxy]acetic acid,
(M) [[3-(2-Amino-1,2-dioxoethyl)-2-cyclopropyl 1-(phenylmethyl)-1H-indol-4-yl]oxy]acetic acid,
(N) [[3-(2-Amino-1,2-dioxoethyl)-1-([1,1'-biphenyl]-2-ylmethyl)-2-cyclopropyl-1H-indol-4-yl]oxy]acetic acid,
(O) 4-[[3-(2-Amino-1,2-dioxoethyl)-2-ethyl-1-(phenylmethyl)-1H-indol-5-yl]oxy]butanoic acid,
(P) mixtures of (A) through (O),
(Q) [8-(Carbomethoxymethyloxy)-2-ethyl-3-(o-phenylbenzyl)indolizin-1-yl]glyoxylamide,
(R) [3-Benzyl-8-(carbethoxymethyloxy)-2-ethylindolizin-1-yl]glyoxylamide,
(S) [8-(Carbethoxymethyloxy)-2-ethyl-3-(o-phenylbenzyl)indolizin-1-yl]glyoxylamide,
(T) [3-Benzyl-8-(carbethoxymethyloxy)-2-methylindolizin-1-yl]glyoxylamide,
(U) [8-(Carbethoxymethyloxy)-3-(m-chlorobenzyl)-2-ethylindolizin-1-yl]glyoxylamide,
(V) [8-Carbethoxymethyloxy-2-ethyl-3-(1-naphthylmethyl)indolizin-1-yl]glyoxylamide,
(W) [3-Benzyl-8-(t-butoxycarbonylmethyloxy)-2-ethylindolizin-1-yl]glyoxylamide,
(X) [8-(Carbmethoxymethyloxy)-2-ethyl-3-(m-trifluoromethylbenzyl)indolizin-1-yl]glyoxylamide,
(Y) [8-(Carbmethoxymethyloxy)-2-cyclopropyl- 3-(o-phenylbenzyl)indolizin-1-yl]glyoxylamide,
(Z) [3-Benzyl-8-(carboxymethyloxy)-2-ethylindolizin-1-yl]glyoxylamide,
(AA) [8-(Carboxymethyloxy)-2-ethyl-3-(o-phenylbenzyl)indolizin-1-yl]glyoxylamide,
(BB) [3-Benzyl-8-(carboxymethyloxy)-2-methylindolizin-1-yl]glyoxylamide,
(CC) [8-(Carboxymethyloxy)-3-(m-chlorobenzyl)-2-ethylindolizin-1-yl]glyoxylamide,
(DD) [8-(Carboxymethyloxy)-2-ethyl-3-(m-trifluoromethylbenzyl)indolizin-1-yl]glyoxylamide,
(EE) [8-Carboxymethyloxy-2-ethyl-3-(1-naphthylmethyl)indolizin-1-yl]glyoxylamide,
(FF) [8-(Carboxymethyloxy)-2-cyclopropyl-3-(o-phenylbenzyl)indolizin-1-yl]glyoxylamide,
(GG) mixtures of (Q) through (FF).

6. A method of treatment of a mammal currently afflicted with a stroke or previously afflicted with a stroke, said method comprising administering to said mammal in need of such treatment a therapeutically effective amount of an N-heterocyclic glyoxylamide compound selected from the formula:

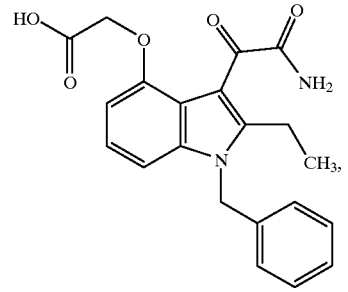

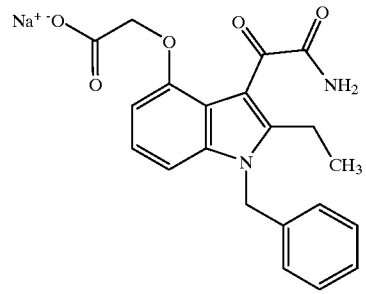

-continued

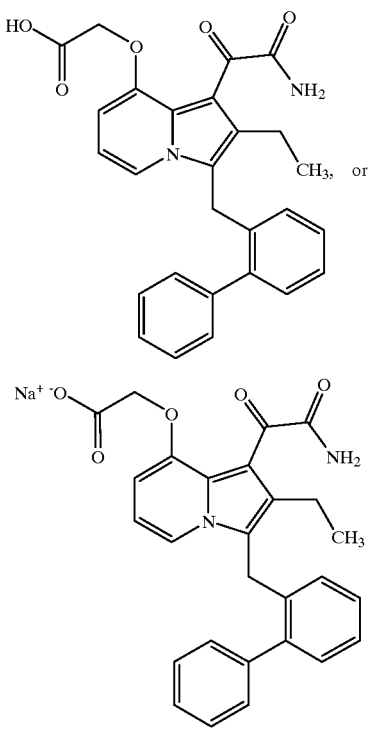

or a prodrug derivative thereof.

7. The method of claim 1 wherein treatment is of a mammal currently afflicted with a stroke, the administering is via a parenteral route and the therapeutically effective amount is a neuronal cell protecting amount.

8. The method of claims 1 wherein the administering is carried out within 6 hours of the onset of the stroke.

9. The method of claims 1 wherein the composition is administered intravenously.

10. The method of claims 1 wherein the compound is administered orally.

11. The method of claims 1 wherein treatment is of a mammal previously afflicted with an ischemic event and the compound is administered in an amount of from 0.01 mg/kg/day to 1000 mg/kg/day.

12. The method of claims 1 wherein the therapeutically effective amount of the compound is in the form of a pharmaceutical formulation comprising the compound and a suitable carrier or excipient therefor.

13. The method of claim 3 wherein for the compound of formula (III) both X are oxygen, only one of $R_{14}$ or $R_{15}$ are -($L_a$)-(acidic group) or -($L_a'$)-(acidic group) and the (acidic group) is carboxyl.

14. The method of claim 2, wherein treatment is of a mammal currently afflicted with a stroke, the administering is via a parenteral route and the therapeutically efective amount is a neuronal cell protecting amount.

15. The method of claim 3, wherein treatment is of a mammal currently afflicted with a stroke, the administering is via a parenteral route and the therapeutically effective amount is a neuronal cell protecting amount.

16. The method of claim 4, wherein treatment is of a mammal currently afflicted with a stroke, the administering is via a parenteral route and the therapeutically efective amount is a neuronal cell protecting amount.

17. The method of claim 5, wherein treatment is of a mammal currently afflicted with a stroke, the administering is via a parenteral route and the therapeutically efective amount is a neuronal cell protecting amount.

18. The method of claim 6, wherein treatment is of a mammal currently afflicted with a stroke, the administering is via a parenteral route and the therapeutically efective amount is a neuronal cell protecting amount.

19. The method of claim 2, wherein the administering is carried out within 6 hours of the onset of the stroke.

20. The method of claim 3, wherein the administering is carried out within 6 hours of the onset of the stroke.

21. The method of claim 4, wherein the administering is carried out within 6 hours of the onset of the stroke.

22. The method of claim 5, wherein the administering is carried out within 6 hours of the onset of the stroke.

23. The method of claim 6, wherein the administering is carried out within 6 hours of the onset of the stroke.

24. The method of claim 2, wherein the composition is administered intravenously.

25. The method of claim 3, wherein the composition is administered intravenously.

26. The method of claim 4, wherein the composition is administered intravenously.

27. The method of claim 5, wherein the composition is administered intravenously.

28. The method of claim 6, wherein the composition is administered intravenously.

29. The method of claim 2, wherein the composition is administered orally.

30. The method of claim 3, wherein the composition is administered orally.

31. The method of claim 4, wherein the composition is administered orally.

32. The method of claim 5, wherein the composition is administered orally.

33. The method of claim 6, wherein the composition is administered orally.

34. The method of claim 2, wherein the treatment is of a mammal previously afflicted with an ischemic event and the compound is administered in an amount of from 0.01 mg/kg/day to 1000 mg/kg/day.

35. The method of claim 3, wherein the treatment is of a mammal previously afflicted with an ischemic event and the compound is administered in an amount of from 0.01 mg/kg/day to 1000 mg/kg/day.

36. The method of claim 4, wherein the treatment is of a mammal previously afflicted with an ischemic event and the compound is administered in an amount of from 0.01 mg/kg/day to 1000 mg/kg/day.

37. The method of claim 5, wherein the treatment is of a mammal previously afflicted with an ischemic event and the compound is administered in an amount of from 0.01 mg/kg/day to 1000 mglkglday.

38. The method of claim 6, wherein the treatment is of a mammal previously afflicted with an ischemic event and the compound is administered in an amount of from 0.01 mg/kg/day to 1000 mg/kg/day.

39. The method of claim 2, wherein the therapeutically effective amount of the compound is in the form of a pharmaceutical formulation comprising the compound and a suitable carrier or excipient therefor.

40. The method of claim 3, wherein the therapeutically effective amount of the compound is in the form of a pharmaceutical formulation comprising the compound and a suitable carrier or excipient therefor.

41. The method of claim 4, wherein the therapeutically effective amount of the compound is in the form of a pharmaceutical formulation comprising the compound and a suitable carrier or excipient therefor.

42. The method of claim 5, wherein the therapeutically effective amount of the compound is in the form of a pharmaceutical formulation comprising the compound and a suitable carrier or excipient therefor.

43. The method of claim 6, wherein the therapeutically effective amount of the compound is in the form of a pharmaceutical formulation comprising the compound and a suitable carrier or excipient therefor.

* * * * *